United States Patent [19]

Sugimori et al.

[11] Patent Number: 4,707,296

[45] Date of Patent: Nov. 17, 1987

[54] ALKOXYETHOXYBENZOIC ACID ESTER DERIVATIVES

[75] Inventors: Shigeru Sugimori; Yasuyuki Goto, both of Kanagawaken, Japan

[73] Assignee: Chisso Corporation, Osaka, Japan

[21] Appl. No.: 933,618

[22] Filed: Nov. 21, 1986

Related U.S. Application Data

[63] This is a continuation-in-part of application Ser. No. 765,440 filed on Aug. 14, 1985, now abandoned.

[51] Int. Cl.$^4$ ............... C09K 19/20; C07C 121/75
[52] U.S. Cl. ............... 252/299.67; 252/299.5; 350/350 R; 558/414; 558/415; 558/416
[58] Field of Search ............... 252/299.67, 299.5; 350/350 R, 350 S; 558/416, 415, 414

[56] References Cited

U.S. PATENT DOCUMENTS

| | | | |
|---|---|---|---|
| 4,158,011 | 6/1979 | Inakai et al. | 252/299.67 |
| 4,198,312 | 4/1980 | Sato et al. | 252/299.67 |
| 4,455,261 | 6/1984 | Sasaki et al. | 252/299.67 |
| 4,502,974 | 3/1985 | Sugimori et al. | 252/299.67 |
| 4,510,069 | 4/1985 | Eidenschink et al. | 252/299.63 |
| 4,564,694 | 1/1986 | Hirai et al. | 252/299.63 |

FOREIGN PATENT DOCUMENTS

| | | | |
|---|---|---|---|
| 57-77658 | 5/1982 | Japan | 252/299.67 |
| 57-142955 | 9/1982 | Japan | 252/299.67 |
| 58-49355 | 3/1983 | Japan | 252/299.67 |
| 58-83665 | 5/1983 | Japan | 252/299.67 |
| 58-136680 | 8/1983 | Japan | 252/299.67 |
| 59-25872 | 2/1984 | Japan | 252/299.67 |
| 59-191789 | 10/1984 | Japan | 252/299.67 |

*Primary Examiner*—Teddy S. Gron
*Attorney, Agent, or Firm*—Wenderoth, Lind & Ponack

[57] ABSTRACT

A novel liquid crystal compound having a large positive dielectric anisotropy value and when added to a liquid crystal composition, forming no deposit in the resulting composition at low temperatures, and a liquid crystal composition containing the same are provided, which compound is an alkoxyethoxybenzoic acid ester derivative expressed by the formula

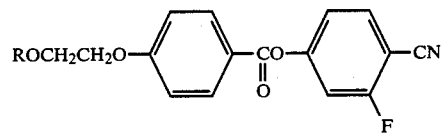

wherein R represents an alkyl group of 1 to 10 carbon atoms.

5 Claims, 2 Drawing Figures

ALKOXYETHOXYBENZOIC ACID ESTER DERIVATIVES

This is a continuation-in-part of application Ser. No. 765,440 filed on Aug. 14, 1985, now abandoned.

BACKGROUND OF THE INVENTION

This invention relates to a novel organic compound having a large, positive dielectric anisotropy value, which is useful as a component of liquid crystal compositions, and a liquid crystal composition containing the same.

Liquid crystal substances and their compositions have been used for various liquid crystal display elements, utilizing the dielectric anisotropy and optical anisotropy of their liquid crystal phases. Their display modes are classified into various ones such as TN type (twisted nematic type), DS type (dynamic scattering type), guest-host type, DAP type, etc. As to liquid crystal substances used therefor, a single liquid crystal compound is difficult to effect liquid crystal display in a suitable temperature range and at low operating voltages when it is filled in a cell; hence practically mixtures of several kinds of liquid crystal compounds and if required, non-liquid crystal compounds have been used to afford improved properties.

The above substances are required to be stable to moisture, heat, air, etc. Further it is desired that they be well compatible with other components used in liquid crystal compositions and the viscosity of the resulting compositions do not increase so much. Still further it is required therefor that the threshold voltage and saturation voltage necessary for driving display elements be as low as possible.

As to compounds to be contained in nematic liquid crystal substances having a positive dielectric anisotropy value, Japanese patent application laid-open No. Sho 58-83665/1983 discloses a compound expressed by the formula

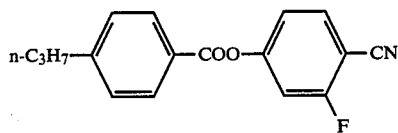

and also discloses that when nematic liquid crystal compositions containing the compound are filled in a cell, the threshold voltage lowers.

However, such liquid crystal compositions containing the compound form deposits at low temperatures. Thus, such compound is not satisfactory as a component of liquid crystal compositions.

Japanese patent application laid-open Nos. Sho 58-136680/1983, Sho 59-25872/1984 and Sho 57-142955/1982 disclose

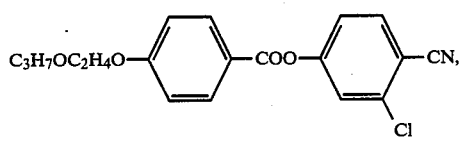

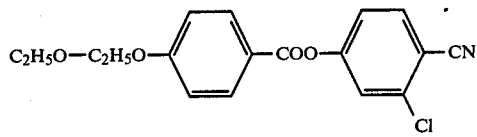

and a compound expressed by the formula

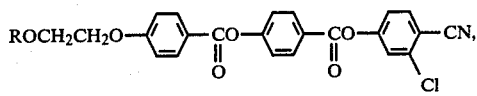

respectively.

The present inventors have made extensive research in order to overcome the above-mentioned problems.

As seen from the foregoing, a first object of the present invention is to provide a novel compound useful as a component of liquid crystal compositions, which compound is well compatible with other components of liquid crystal compositions, forms no deposit in liquid crystal compositions containing it at low temperatures and when added as a component of liquid crystal compositions, the threshold voltage of the resulting compositions is reduced. A second object of the present invention is to provide a compound useful as a component of a liquid crystal composition having a lower viscosity, particularly a lower viscosity at lower temperatures as compared with those using as a component, compounds as disclosed in the prior art (such as

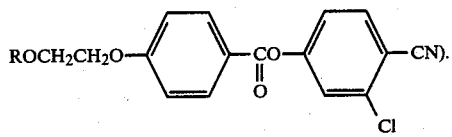

A third object of the present invention is to provide a novel liquid crystal composition containing the above compound.

SUMMARY OF THE INVENTION

The present invention resides in a 3-fluoro-4-cyanophenyl 4-(β-alkoxyethoxy)benzoate expressed by the formula

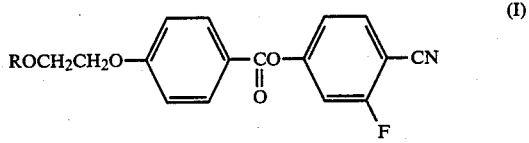

wherein R represents an alkyl group of 1 to 10 carbon atoms, and a liquid crystal composition containing at least one member of compounds expressed by the formula (I).

DETAILED DESCRIPTION OF THE PREFERRED EMBODIMENTS

Figure 1:
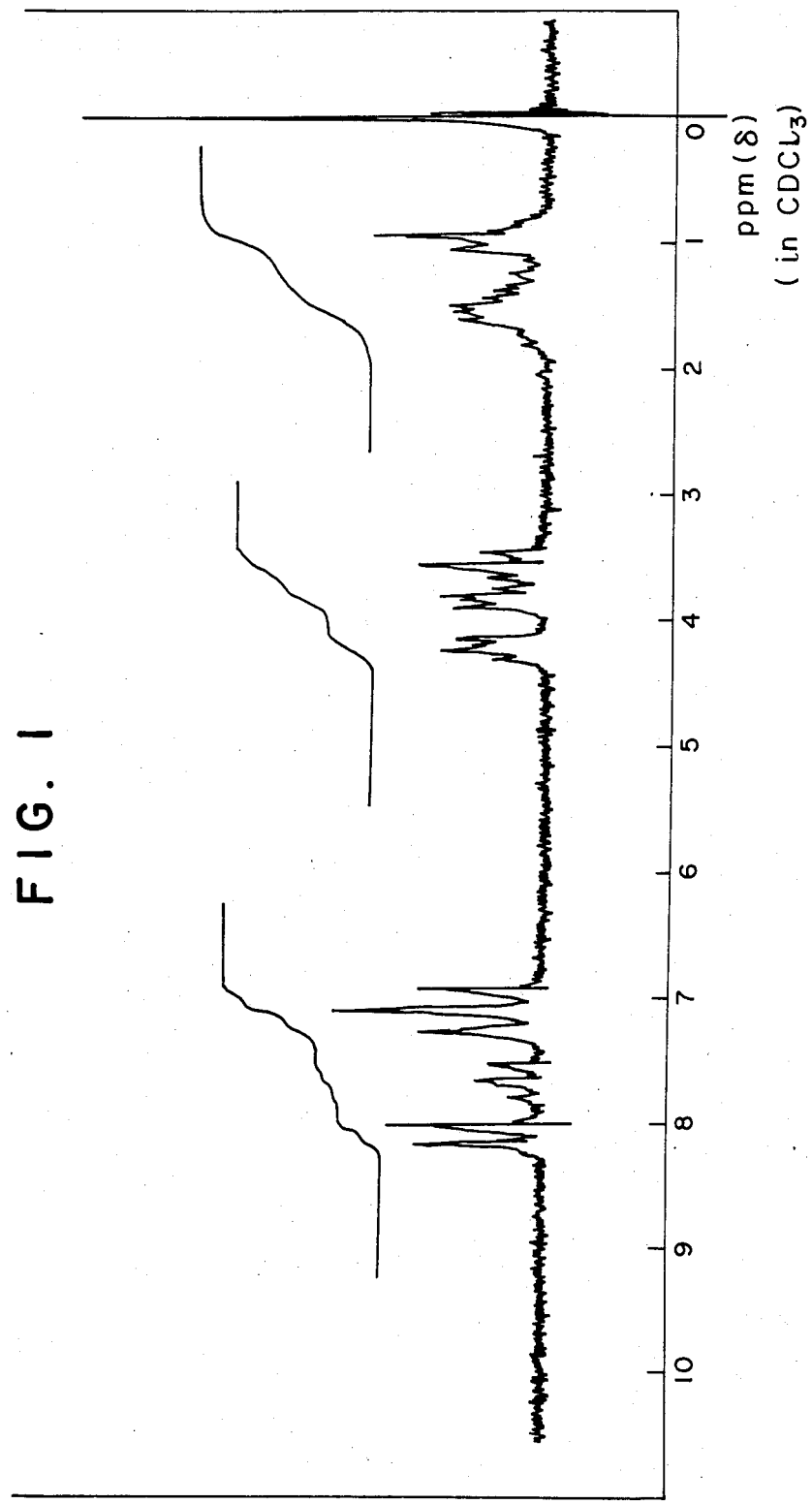
FIG. 1 shows a NMR chart of the compound of the present invention (R=C$_4$H$_9$ in the formula (I)).

Examples of R in the formula (I) are linear chain alkyl group such as methyl, ethyl, propyl, butyl, pentyl, hexyl, heptyl, octyl, nonyl and decyl and branched chain alkyl group such as isopropyl, 1-methylpropyl, isobutyl, 1-methylbutyl, 2-methylbutyl, isopentyl, 1-methylpentyl, 1-ethylpentyl, 2-methylpentyl, 1-methylhexyl, 2-ethylhexyl, 1-methylheptyl, etc.

R in the formula (I) is preferred to be an alkyl group of 1 to 6 carbon atoms.

Preparation of the compound of the present invention will be illustrated below by the following reaction equation:

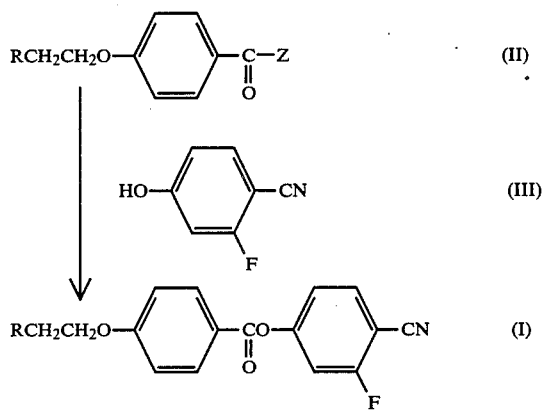

In this equation, R is as defined above and Z represents a halogen atom.

As shown by the above equation, it is possible to prepare a 3-fluoro-4-cyanophenyl 4-(β-alkoxyethoxy)-benzoate (I) from a 4-(β-alkoxyethoxy)benzoyl halide (II) and 3-fluoro-4-cyanophenyl (III). The halogen atom (Z) in the formula (II) is preferably chlorine. The reaction of a compound of the formula (II) with a compound of the formula (III) may be carried out in an inert organic solvent. Examples of such an inert solvent are diethyl ether, tetrahydrofuran, dimethylformamide, benzene, toluene, etc. A basic substance such as a tertiary amine, e.g. pyridine, triethylamine, etc. may be added to the inert solvent. The reaction may be carried out under the atmospheric pressure. Further the reaction may be carried out in the range of room temperature and a reflux temperature of the reaction mixture.

The compound of the formula (II) may be obtained as shown in the following reaction equations:

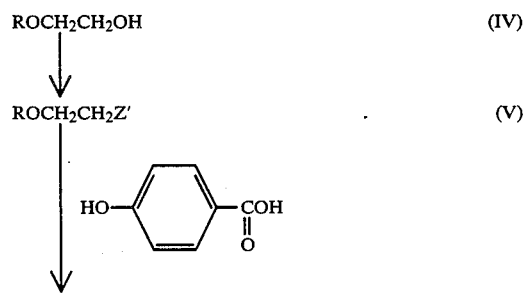

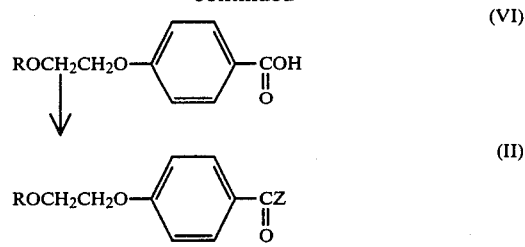

In the above equations, R and Z are as defined above and Z' represents a halogen atom.

First, an ethylene glycol monoalkyl ether (IV) is halogenated to prepare a 2-alkoxyethyl halide (V). As a halogenating agent, phosphorus tribromide, phosphorus trichloride or the like may be used. Preferred halogen atom of the halogenating agent is bromine atom, which makes easy the subsequent etherification reaction. Next, from a compound of the formula (V) and hydroxybenzoic acid is obtained a 4-(β-alkoxyethoxy)benzoic acid (VI), from which an acid halide compound (II) is obtained. For halogenating the compound of the formula (VI), thionyl chloride may be used.

The liquid crystal composition of the present invention contains at least one member of the compounds expressed by the formula (I) in a quantity of preferably 1 to 30% by weight, more preferably 5 to 20% by weight. If the content is less than 1% by weight, its contribution to reduction in driving voltage is small, while it exceeds 30% by weight, the viscosity of the resulting composition increases.

Examples of liquid crystal compounds usable in the composition of the present invention together with the compound of the present invention are compounds belonging to the following groups expressed by the formulas (i)–(xxxiii) wherein A and A' each represent alkyl group, Y represents alkyl group, cyano group or halogen atom and X represents

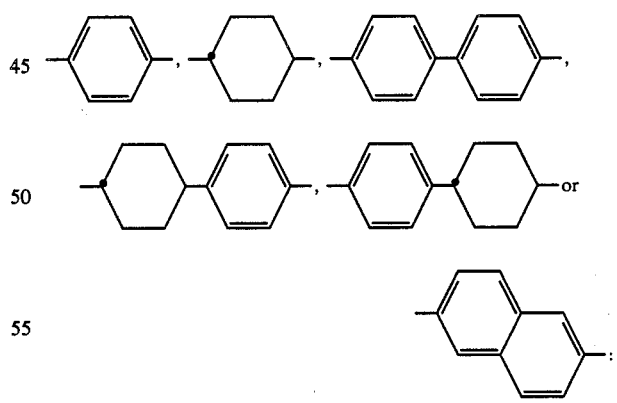

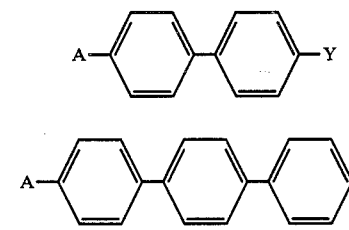

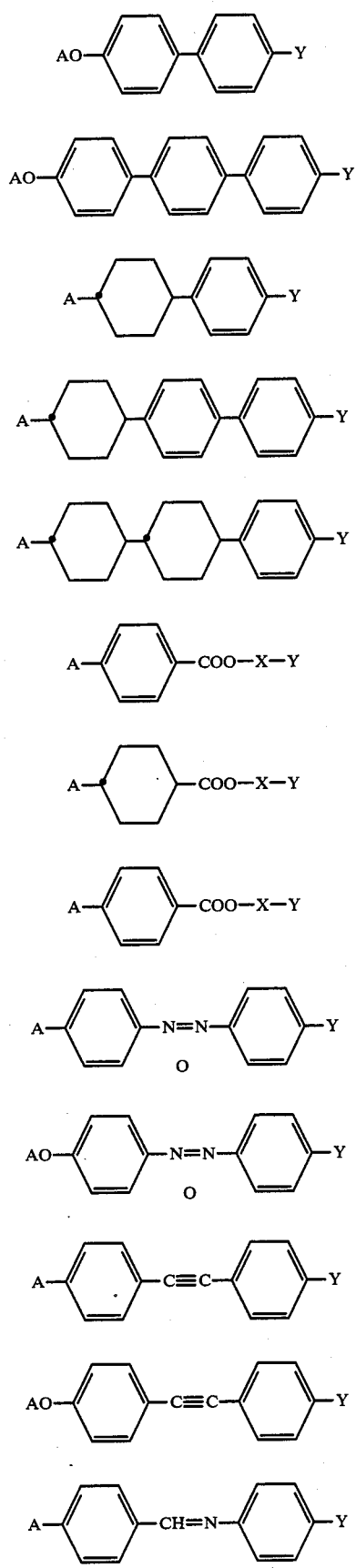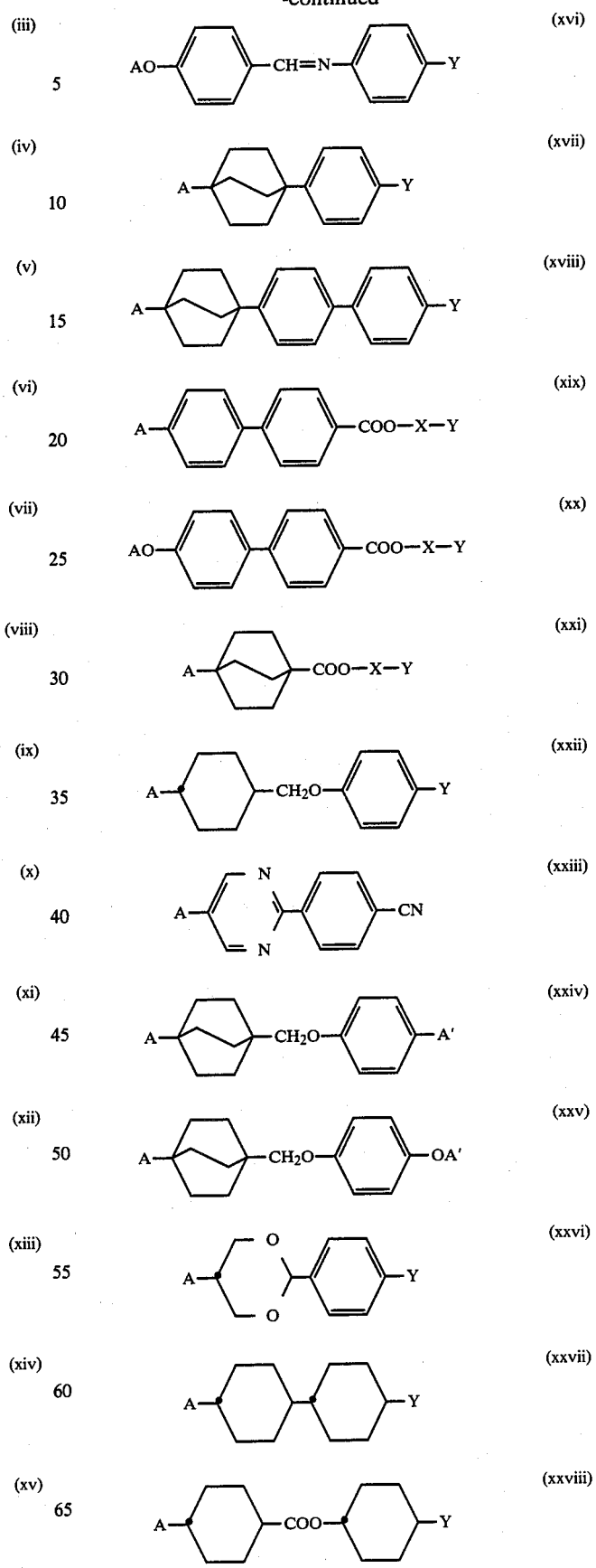

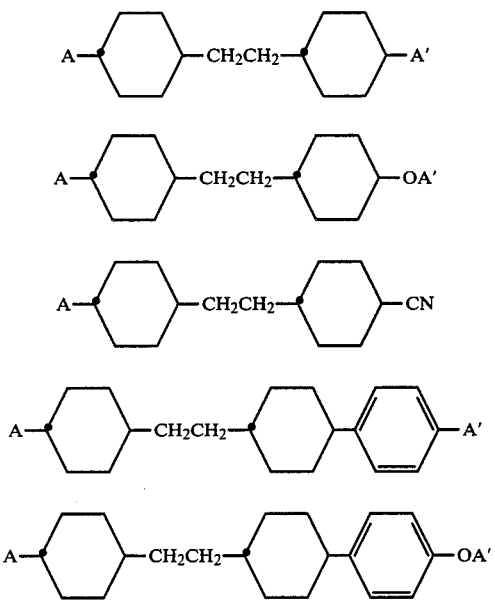

(xxix)
(xxx)
(xxxi)
(xxxii)
(xxxiii)

The compounds of the present invention, the 3-fluorocyanophenyl esters, are novel and can be effectively used as a component constituting liquid crystal compositions.

The compounds of the present invention exhibit a large, positive dielectric anisotropy value ($\Delta\epsilon$) (obtained by extrapolation method) and when they are added to nematic liquid crystal compositions and the mixture is filled in a cell, it is possible to reduce the threshold voltage of the resulting liquid crystal cell. Further, the compounds of the present invention are well compatible with other components of liquid crystal compositions, and the resulting liquid crystal compositions form no deposit in low temperature range.

Next, preparation and use application of a compound of the present invention will be described in more detail by way of Example and Application example, respectively.

The liquid crystal composition containing the compound of the present invention exhibits a lower viscosity at low temperatures as compared with that ($A_{2a}$) containing 3-chloro-4-cyanophenyl 4-($\beta$-butoxyethoxy)benzoate described in Comparative application example 1, and can be applied to liquid crystal display elements capable of being driven at a low Vth. Further, the liquid crystal composition containing the compound of the present invention is difficultly deposited as compared with the liquid crystal composition ($A_{2b}$) containing 3-chloro-4-cyanophenyl 4-propyl benzoate described in Comparative application example 2; thus it can be applied to liquid crystal display elements capable of being driven at a low Vth.

EXAMPLE 1

3-Fluoro-4-cyanophenyl 4-($\beta$-ethoxyethoxy)benzoate

To a solution of 3-fluoro-4-cyanophenol (1.5 g, 11 mmols) dissolved in dry pyridine (5 cc) was added a solution of 4-($\beta$-ethoxyethoxy)benzoic acid chloride (2.5 g, 11 mmols) dissolved in dry toluene (10 cc), followed by heating the mixture with stirring at 60° C. for 3 hours, thereafter adding it to water (100 cc), washing the resulting separated toluene layer with 6N-hydrochloric acid, 2N-NaOH aqueous solution and water, in this order, drying over anhydrous sodium sulfate, distilling off toluene from the toluene layer and recrystallizing the resulting oily residue from ethyl alcohol (10 cc) to obtain the objective 3-fluoro-4-cyanophenyl 4-($\beta$-ethoxyethoxy)benzoate (2.1 g) (yield: 64%).

This compound had a m.p. of 62.4°–63.2° C. and its nematic-clearing point was 8.1° C. in terms of calculated value by way of extrapolation of a model of additive property.

EXAMPLE 2

3-Fluoro-4-cyanophenyl 4-($\beta$-butoxyethoxy)benzoate

Example 1 was repeated except that 4-($\beta$-ethoxyethoxy)benzoic acid was replaced by 4-($\beta$-butoxyethoxy)benzoic acid, to obtain 3-fluoro-4-cyanophenyl 4-($\beta$-butoxyethoxy)benzoate. The properties of this product are shown in Table 1 together with the compound obtained in Example 1. Further, the NMR chart of this product is shown in FIG. 1.

COMPARATIVE EXAMPLE 1

Example 2 was repeated except that the compound of the formula (III) was replaced by 3-chloro-4-cyanophenol to obtain 3-chloro-4-cyanophenyl 4-($\beta$-butoxyethoxy)benzoate. The properties of this product are shown in Table 1.

TABLE 1

| No. | Compound | M.P. °C. | Nematic-clearing point (calculated value) °C. |
|---|---|---|---|
| Ex. 1 | $C_2H_5OCH_2CH_2O$—⟨⟩—CO—⟨⟩—CN (F) | 62.4 –63.2 | 8.1 |
| Ex. 2 | $C_4H_9OCH_2CH_2O$—⟨⟩—CO—⟨⟩—CN (F) | 48.6 | −13.3 |
| Comp. ex. 1 | $C_4H_9OCH_2CH_2O$—⟨⟩—CO—⟨⟩—CN (Cl) | 42.3 | −54.0 |

APPLICATION EXAMPLE 1

A nematic liquid crystal composition (A) consisting of

| Structure | Weight % |
|---|---|
| $C_3H_7$—⟨cyclohexyl⟩—⟨phenyl⟩—CN | 24% by weight, |
| $C_5H_{11}$—⟨cyclohexyl⟩—⟨phenyl⟩—CN | 36% by weight, |
| $C_7H_{15}$—⟨cyclohexyl⟩—⟨phenyl⟩—CN | 25% by weight, and |
| $C_5H_{11}$—⟨cyclohexyl⟩—⟨phenyl⟩—⟨phenyl⟩—CN | 15% by weight, | has a dielectric anisotropy value (hereinafter abbreviated to $\Delta\epsilon$) of 11.6, a nematic-clearing point of 72.0° C. and a viscosity at 20° C. of 28 cp. When this composition (A) was filled in a TN cell composed of opposed transparent electrodes subjected to aligning treatment (the distance between the electrodes: 10 μm), the resulting well exhibited an operation threshold voltage of 1.75 V and a saturation voltage of 2.40 V.

A liquid crystal composition ($A_{1a}$) consisting of the above liquid crystal composition (A) (85 parts by weight) and 3-fluoro-4-cyanophenyl 4-(β-ethoxyethoxy)benzoate prepared in Example 1 (15 parts by weight) and a $\Delta\epsilon$ of 16.0, a nematic-clearing point of 62.4° C. and a viscosity at 20° C. of 38 cp.

When this composition ($A_{1a}$) was filled in the same TN cell as above, the resulting cell exhibited an operation threshold voltage of 1.22 V and a saturation voltage of 1.80 V. When this composition ($A_{1a}$) was allowed to stand at −20° C. for one month, no deposit was formed.

The properties are shown in Table 2.

APPLICATION EXAMPLE 2

Figure 2:
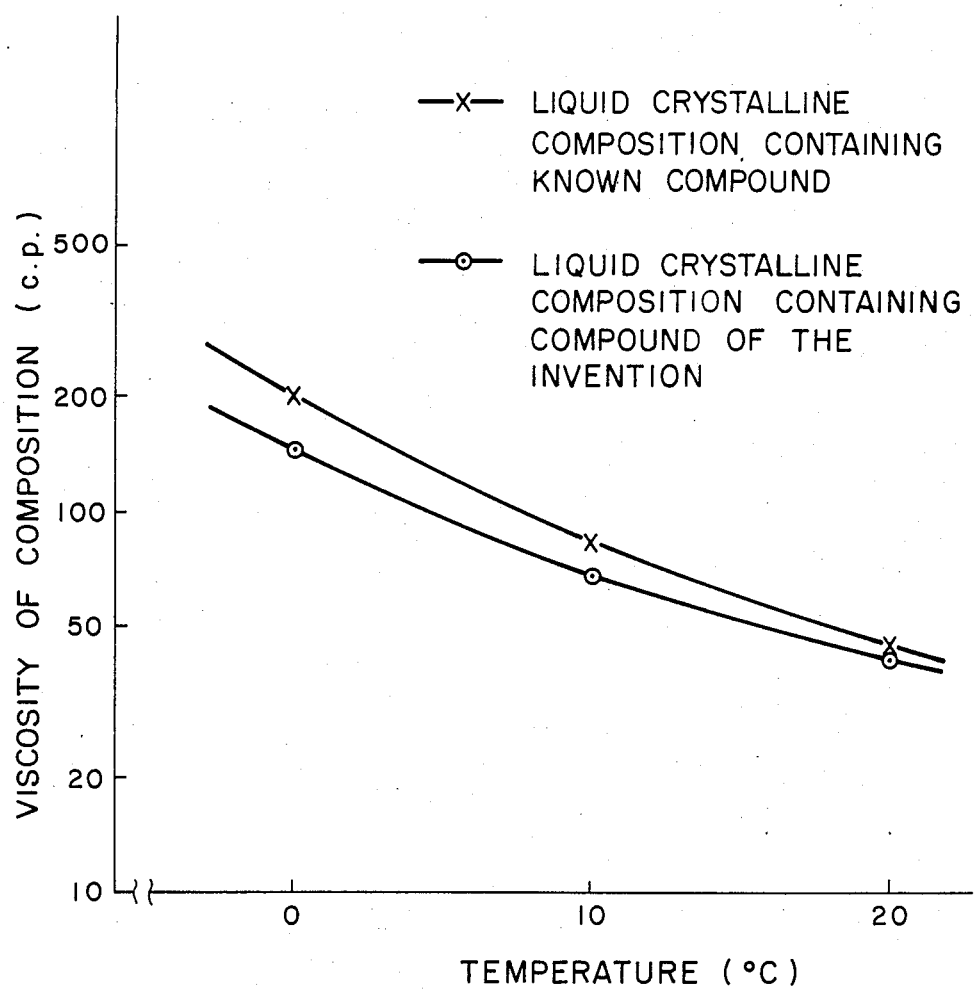
FIG. 2 shows a chart illustrating the respective temperature-viscosity relationships of a liquid crystal composition containing a compound of the present invention (wherein R=C$_4$H$_9$ in the formula (I)) and that containing a compound of the prior art (R=C₄H₉ and Cl in place of F in the formula (I)).

3-Fluoro-4-cyanophenyl 4-(β-butoxyethoxy)benzoate (15 parts by weight) prepared in Example 2 was blended with the above nematic liquid crystal composition (A) (85 parts by weight). The properties of the resulting liquid crystal composition ($A_{1b}$) were measured in the same manner as in Application example 1. The results are shown in Table 2. Further, the temperature-viscosity relationship thereof is shown in FIG. 2.

COMPARATIVE APPLICATION EXAMPLE 1

3-Chloro-4-cyanophenyl 4-(β-butoxyphenyl)benzoate (15 parts by weight) was blended with the above composition (A) (85 parts by weight). The properties of the resulting liquid crystal composition ($A_{2a}$) were measured in the same manner as in Application example 1. The results are shown in Table 2. Further, the temperature-viscosity relationship thereof is shown in FIG. 2.

COMPARATIVE APPLICATION EXAMPLE 2

A liquid crystal composition ($A_{2b}$) consisting of the above nematic liquid crystal composition (A) described in Application example 1 (85 parts by weight) and 3-fluoro-4-cyanophenyl 4-propylbenzoate (15 parts by weight) exhibited a $\Delta\epsilon$ of 16.3, a nematic-clearing point of 63.8° C. and a viscosity at 20° C. of 33.2 cp. When this composition ($A_{2b}$) was filled in the same TN cell as above, the resulting cell exhibited an operation threshold voltage of 1.33 V and a saturation voltage of 1.86 V. This composition ($A_{2b}$) formed deposits at −20° C. The properties are shown in Table 2.

TABLE 2

| No. | Composition | parts by weight | Transition point C—N (°C.) | Transition point N—I (°C.) | $\Delta\epsilon$ | $\Delta n$ | viscosity (c.p.) | | $V_{th}$ (10μm TN cell) (V) | $V_{sat}$ (10μm TN cell) (V) |
|---|---|---|---|---|---|---|---|---|---|---|
| | Composition (A) | | <−20 | 72.0 | 11.6 | 0.140 | 28 | (20° C.) | 1.75 | 2.40 |
| Application ex. 1 | Composition (A) $C_2H_5OCH_2CH_2O$—⟨phenyl⟩—CO—⟨phenyl(F)⟩—CN | 85 15 | | 62.4 | 16.0 | 0.134 | 38 | (20° C.) | 1.22 | 1.80 |
| Application ex. 2 | Composition (A) $C_4H_9OCH_2CH_2O$—⟨phenyl⟩—CO—⟨phenyl(F)⟩—CN | 85 15 | | 60.2 | 14.2 | 0.133 | 40.0 68.0 149.0 | (20° C.) (10° C.) (0° C.) | 1.27 | 1.93 |
| Compar. appln. ex. 1 | Composition (A) $C_4H_9OCH_2CH_2O$—⟨phenyl⟩—CO—⟨phenyl(Cl)⟩—CN | 85 15 | | 56.1 | 13.7 | 0.128 | 45.0 84.0 200.3 | (20° C.) (10° C.) (0° C.) | 1.29 | 1.95 |

TABLE 2-continued

| No. | Composition | parts by weight | Transition point C—N (°C.) | Transition point N—I (°C.) | Δε | Δn | viscosity (c.p.) | $V_{th}$ (10μm TN cell) (V) | $V_{sat}$ (10μm TN cell) (V) |
|---|---|---|---|---|---|---|---|---|---|
| Compar. appln. ex. 2 | Composition (A) C₃H₇—⌬—CO—⌬—CN, F | 85 15 | >−20 | 63.8 | 16.3 | 0.140 | 33.2 (20° C.) | 1.33 | 1.86 |

What we claim is:

1. A 3-fluoro-4-cyanophenyl 4-(β-alkoxyethoxy)benzoate expressed by the formula

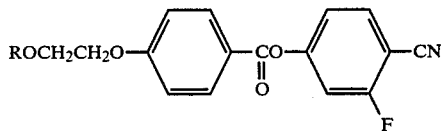

wherein R represents an alkyl group of 1 to 10 carbon atoms.

2. A compound according to claim 1 wherein R in said formula represents an alkyl group of 1 to 6 carbon atoms.

3. The compound of claim 1 which has the formula

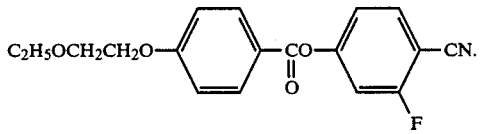

4. The compound of claim 1 which has the formula

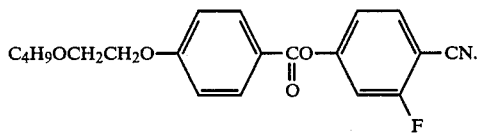

5. A liquid crystal composition having at least two components at least one of which is a compound set forth in claim 1.

* * * * *